US012458226B2

(12) United States Patent
Charles

(10) Patent No.: US 12,458,226 B2
(45) Date of Patent: Nov. 4, 2025

(54) SURGICAL CONTACT LENS FOR OPHTHALMIC PROCEDURES

(71) Applicant: Alcon Inc., Fribourg (CH)

(72) Inventor: Steven T. Charles, Memphis, TN (US)

(73) Assignee: Alcon Inc., Fribourg (CH)

( * ) Notice: Subject to any disclaimer, the term of this patent is extended or adjusted under 35 U.S.C. 154(b) by 260 days.

(21) Appl. No.: 18/329,943

(22) Filed: Jun. 6, 2023

(65) Prior Publication Data

US 2023/0414099 A1 Dec. 28, 2023

Related U.S. Application Data

(60) Provisional application No. 63/367,154, filed on Jun. 28, 2022.

(51) Int. Cl.
*A61B 3/125* (2006.01)

(52) U.S. Cl.
CPC .................................... *A61B 3/125* (2013.01)

(58) Field of Classification Search
CPC ............. A61B 3/125; A61B 2017/3492; A61F 2009/0052; A61F 2220/0008; A61F 9/007; A61F 9/00736; A61F 9/009; A61F 9/0017
See application file for complete search history.

(56) References Cited

U.S. PATENT DOCUMENTS

| | | | | |
|---|---|---|---|---|
| 3,971,073 | A | 7/1976 | Richards et al. | |
| 3,996,626 | A | 12/1976 | Richards et al. | |
| 4,012,823 | A | 3/1977 | Richards | |
| 4,262,370 | A | 4/1981 | Hartstein | |
| 4,275,733 | A * | 6/1981 | Marinoff ............ | A61B 17/0231 606/107 |
| 5,817,099 | A | 10/1998 | Skolik et al. | |
| 7,480,956 | B2 | 1/2009 | Policicchio et al. | |
| 7,803,726 | B2 | 9/2010 | Policicchio et al. | |
| 8,062,260 | B2 | 11/2011 | McCawley | |
| 8,678,593 | B2 | 3/2014 | Abt | |
| 9,339,184 | B2 | 5/2016 | Hassan et al. | |
| 9,554,702 | B2 | 1/2017 | Papac | |
| 9,895,264 | B2 | 2/2018 | John et al. | |
| 10,335,315 | B2 | 7/2019 | Goldshleger et al. | |
| 10,413,178 | B2 | 9/2019 | Graham et al. | |
| 10,905,462 | B2 | 2/2021 | Ochoa | |
| 11,039,746 | B1 | 6/2021 | Benner | |
| 2005/0288697 | A1* | 12/2005 | Tei ........................ | A61F 9/0017 606/166 |
| 2006/0041308 | A1* | 2/2006 | Nichamin ............. | A61F 2/1613 623/6.43 |
| 2012/0099077 | A1* | 4/2012 | Abt ......................... | A61F 9/009 351/219 |

(Continued)

FOREIGN PATENT DOCUMENTS

| | | |
|---|---|---|
| WO | 2017045986 A1 | 3/2017 |

*Primary Examiner* — Andrew Restaino

(57) ABSTRACT

A lens holder for an ophthalmic procedure is provided. The lens holder includes: a rim configured to hold a lens; and a flange coupled to the rim, the flange including a first surface configured to be positioned on an ocular surface of an eye and an opposing second surface. The flange includes one or more conjunctiva capture features extending from the first surface to the second surface of the flange, and the one or more conjunctiva capture features are configured to be latched on to one or more portions of conjunctiva of the eye.

12 Claims, 4 Drawing Sheets

(56) References Cited

U.S. PATENT DOCUMENTS

| | | | |
|---|---|---|---|
| 2016/0296221 | A1 | 10/2016 | Morris |
| 2019/0357768 | A1 | 11/2019 | Shareef |
| 2021/0128195 | A1 | 5/2021 | Abt |

* cited by examiner

SURGICAL CONTACT LENS FOR OPHTHALMIC PROCEDURES

BACKGROUND

A surgical contact lens can be positioned on a patient's eye during an ophthalmic surgical procedure of the posterior segment of the eye to allow for viewing the patient's retina (e.g., peripheral retina) during the procedure. A challenge related to using surgical contact lenses is maintaining a position of the surgical contact lens on the patient's eye during the procedure. One solution has been to have an assistant manually maintain the position of the surgical contact lens during the procedure. This solution requires the assistant to be highly trained. Further, any repositioning of the surgical contact lens by the assistant slows down the procedure being performed. Another solution has been to suture a portion of the surgical contact lens to the patient's eye. While this solution can successfully maintain the position of the surgical contact lens over the patient's eye, even a small suture is an injury to the patient's eye, and a less invasive process for maintaining the position of the surgical contact lens over the patient's eye would be beneficial.

Therefore, an improved surgical contact lens and related method for maintaining a position of a surgical contact lens over a patient's eye is needed.

SUMMARY

In certain embodiments, a lens holder for an ophthalmic procedure is provided. The lens holder includes: a rim configured to hold a lens; and a flange coupled to the rim, the flange including a first surface configured to be positioned on an ocular surface of an eye and an opposing second surface. The flange includes one or more conjunctiva capture features extending from the first surface to the second surface of the flange, and the one or more conjunctiva capture features are configured to be latched on to one or more portions of conjunctiva of the eye.

In certain embodiments, a surgical contact lens for an ophthalmic procedure is provided. The surgical contact lens includes: a rim; a lens positioned inside the rim; and a flange coupled to the rim, the flange including a first surface configured to be positioned on an ocular surface of an eye and an opposing second surface. The flange includes one or more conjunctiva capture features extending from the first surface to the second surface of the flange, and the one or more conjunctiva capture features are configured to be latched on to one or more portions of conjunctiva of the eye.

In certain embodiments, a method of securing a contact lens holder to an eye is provided. The method includes: positioning a lens holder on an ocular surface of an eye, the lens holder comprising: a first surface contacting the eye and an opposing second surface, and one or more conjunctiva capture features extending from the first surface to the second surface; and pulling one or more portions of conjunctiva into at least one of the one or more conjunctiva capture features.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Embodiments of the present disclosure generally relate to a surgical contact lens including a lens holder and a lens, and related methods for using the surgical contact lens. As used herein, a surgical contact lens refers to an optical device that includes a lens holder and a lens (i.e., a transparent optical component configured to focus or disperse light) positioned in the lens holder.

The disclosed surgical contact lens comprises a lens holder having one or more conjunctiva capture features (e.g., a slot or opening). Once the lens holder is positioned on a patient's eye during an ophthalmic procedure, one or more portions of the conjunctiva of the patient's eye can be moved (e.g., pulled) into or through the one or more conjunctiva capture features on the lens holder. Moving each portion of conjunctiva into or through the respective one or more conjunctiva capture features of the lens holder latches the corresponding portion(s) of conjunctiva to the lens holder of the surgical contact lens, which helps with securing and maintaining the position of the surgical contact lens in relation to the eye during the procedure. After the procedure is completed, the portion(s) of conjunctiva are removed from the conjunctiva capture feature(s), and the surgical contact lens is removed from the patient's eye. Therefore, the disclosed surgical contact lens allows for maintaining the position of the surgical contact lens during the procedure without use of an assistant or more invasive procedures, such as suturing a surgical contact lens to a patient's eye.

Further, the disclosed lens holder is configured to hold one of a number of different lenses while the lens holder remains latched to a patient's eye, thereby enabling different views of the patient's eye without any repositioning of the lens holder on the patient's eye. For example, while the lens holder remains latched by one or more portions of the conjunctiva, a first lens in the lens holder can be replaced with a second lens in the lens holder to allow for providing a different view of the patient's eye without any repositioning of the lens holder on the patient's eye.

Figure 1A:
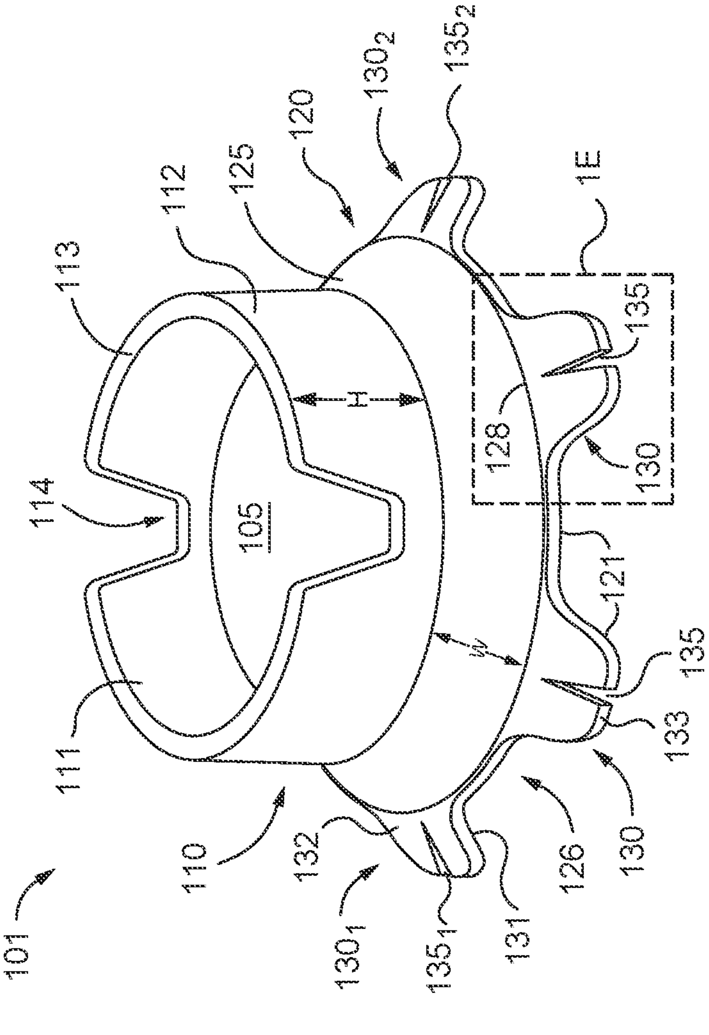
FIG. 1A illustrates a lens holder for a surgical contact lens, according to certain embodiments.

FIG. 1A illustrates a lens holder 101 for a surgical contact lens, according to certain embodiments. As described below in reference to FIG. 1B, the lens holder 101 (see FIGS. 1A and 1B) is used as part of a surgical contact lens 100 (see FIG. 1B). As part of the surgical contact lens 100, the lens holder 101 can be used to retain a lens, such as the lens 150 shown in FIG. 1B, for viewing a patient's eye during a procedure. In certain embodiments, lens 150 may be referred to as a macular lens for viewing the central area of the retina.

The lens holder 101 includes a rim 110 and a flange 120 connected to and disposed around the rim 110. The flange 120 extends outwardly from the rim 110. In certain embodiments, the height ("H") of the flange 120 may be between 3-4 millimeters (mm). In certain embodiments, the width ("W") of the rim 110 may be between 1-2 mms. A lower surface 121 of the flange 120 is configured to be positioned on a patient's eye during an optical procedure. In certain embodiments, the flange 120 is made flexible such as to conform to the somewhat irregular surface of the conjunctiva. As the eye deforms when it is moved in various directions by the surgeon to view the peripheral retina and to work with various instruments, the flexibility of the flange 120 allows flange 120 to maintain its position on the eye. The rim 110 surrounds an inner opening 105 of the lens holder 101. The inner opening 105 allows for viewing the patient's eye during a procedure when a lens is positioned inside the lens holder 101.

The rim 110 includes an inner surface 111, an outer surface 112, and a top surface 113 connecting the inner surface 111 with the outer surface 112. The top surface 113 of the rim 110 includes one or more recesses 114. In the recesses 114, the top surface 113 of the rim 110 can extend downward towards the flange 120. When a lens (e.g., lens 150 in FIG. 1B) is positioned in the lens holder 101, the extension of the recesses 114 towards the flange 120 allows for easier insertion and removal of the lens from the lens holder 101. For example, when a lens (e.g., lens 150 in FIG. 1B) is positioned in the lens holder 101, the recesses 114 allow for some portions of the lens to be exposed, thereby allowing a surgical instrument, such as forceps, to grab the exposed portions or edges of the lens and remove the lens. Similarly, placing the lens in the lens holder 101 can be more easily performed because the recesses 114 provide openings for the forceps to more effectively position and center the lens into the lens holder 101. Note that the shape of the recesses 114 in FIG. 1A is only one example of how recesses 114 can be provided on the rim 110 and that recesses can have a variety of shapes (e.g., U-shaped, half-circles, V-grooves, etc.). In addition, although only two recesses 114 are shown in FIG. 1A, a fewer or larger number of recesses 114 are also in the scope of the disclosure.

The flange 120 can include a base 125 (also referred to as ring portion) and a plurality of tabs 130 connected to the base 125. The base 125 of the flange 120 can be connected to the rim 110. The plurality of tabs 130 can extend outwardly from an outer edge 128 of the base 125. The length of each tab 130 measured from the edge of the flange 120 is about 1-2 mms. The plurality of tabs 130 can each include a lower surface 131, an upper surface 132, and a side surface 133 connecting the lower surface 131 with the upper surface 132. The lower surface 121 of the flange 120, including the lower surface 131 of the tabs 130, is configured to contact a patient's eye during a procedure. The lower surface 121 of the flange 120 can have a curvature that corresponds to (1) an average corneal curvature, (2) a corneal curvature of a particular patient, or (3) an average corneal curvature associated with a group of patients.

Each tab 130 can include a slot 135 or other conjunctiva capture feature that is configured to retain a portion of conjunctiva as described in further detail below. In FIG. 1A, the slots 135 are shown as V-shaped slots, but any conjunctiva capture feature that is configured to capture and retain (e.g., pinch, latch, hold, etc.) the conjunctiva can be used. As shown, the slots 135 can extend from the lower surface 131 to the upper surface 132. Furthermore, the slots 135 can extend out to the side surface 133. In one embodiment, a portion of the conjunctiva can be pulled up above the upper surface 132 of one of the tabs 130, for example using a syringe or micro forceps, and then the portion of the conjunctiva can be positioned into the slot 135 of that tab 130. Once positioned into the slot 135, the portion of the conjunctiva is held in place by the slot 135.

The flange 120 can further include a recessed portion 126 between each neighboring pair of tabs 130. The recessed portions 126 can be used to allow access to the patient's eye during the procedure, for example to allow insertion of a surgical tool (e.g., a trocar cannula) into the patient's eye during a procedure. Note that the shapes of recesses 114 in FIG. 1A are exemplary and that recesses 114 may be shaped differently in different embodiments. For example, in the embodiments of FIG. 1B, recesses 114 are U-shaped.

Figure 1C:
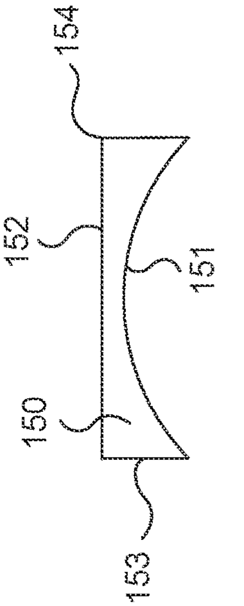
FIG. 1C illustrates a side view of the lens shown in FIG. 1B, according to certain embodiments.
Figure 1D:
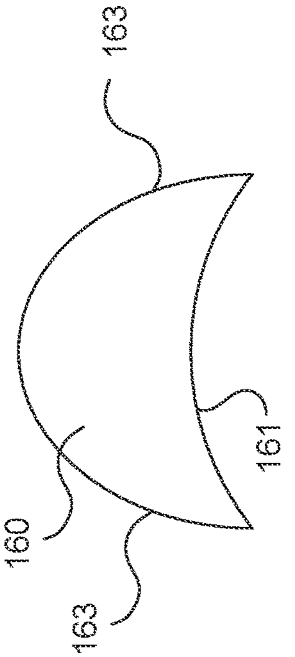
FIG. 1D illustrates a side view of an example wide-angle lens, according to certain embodiments.
Figure 1B:
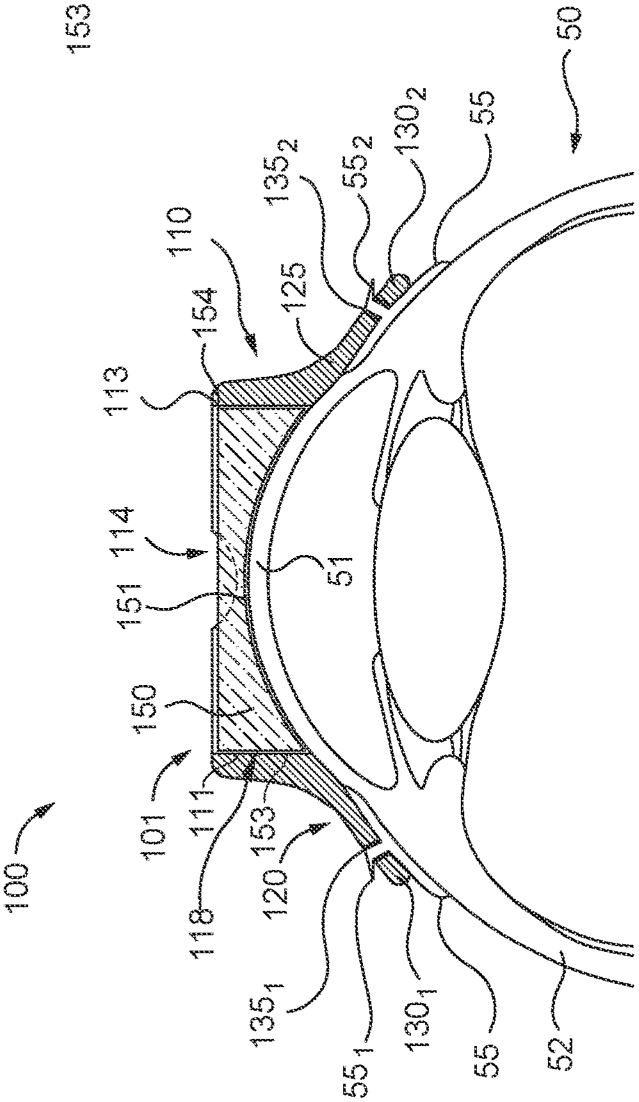
FIG. 1B illustrates a side cross-sectional view of a surgical contact lens positioned on an eye, according to certain embodiments.

FIG. 1B illustrates a side cross-sectional view of an example surgical contact lens 100 positioned on an eye 50, according to certain embodiments. The surgical contact lens 100 includes the lens holder 101 described above in reference to FIG. 1A and a lens 150 positioned inside the lens holder 101. The view in FIG. 1B can be taken along a cross-section that extends through the first tab $\mathbf{130}_1$ and the second tab $\mathbf{130}_2$ of the lens holder 101 shown in FIGS. 1A and 1B. The surgical contact lens 100 that includes the lens 150 can be used to view an interior of a patient's eye 50 (e.g., central portion of the retina) during an ophthalmic surgical procedure. As described further below, the lens 150 is removable and exchangeable. For example, to view the peripheral portions of the retina, the surgeon may remove the lens 150 and replace it with a wide-angle lens 160 shown in FIG. 1D.

In FIG. 1B, the gaps (e.g., gap 118) shown between the inner surface 111 and side surfaces 153 of lens 150 in FIG. 1B are to illustrate that the lens 150 and the lens holder 101 are separate components. Therefore, in certain embodiments, the size of such gaps may be larger or smaller and such gaps are shown for illustration purposes only. Further, although in the embodiments of FIGS. 1A and 1B, the lens holder 101 and any lens positioned in the lens holder 101 are separate components, in certain other embodiments, a lens may be affixed to or permanently positioned in and coupled to the lens holder 101.

FIG. 1C illustrates a side view of the lens 150, according to certain embodiments. The lens 150 can be positioned inside the lens holder 101 as shown in FIG. 1B. The lens 150 includes a bottom surface 151, a top surface 152, and a side surface 153 connecting the bottom surface 151 with the top surface 152. The bottom surface 151 can have a curvature configured to conform to an average corneal curvature, a corneal curvature of a particular patient, or an average corneal curvature associated with a group (e.g., children of a particular age) of patients. The top surface 152 of the lens can connect to the side surface 153 at an edge 154.

The bottom surface 151 of the lens 150 can contact the eye 50 during a procedure. For example, as shown in FIG. 1B, the bottom surface 151 of the lens 150 can contact the cornea 51 of the eye 50. The conjunctiva 55 of the patient's eye begins where the cornea 51 ends. The conjunctiva 55 is located over the sclera 52 of the eye 50. The conjunctiva 55 is also connected to the eyelids, which are not shown for ease of illustration. The conjunctiva 55 is a thin tissue of the eye 50 having a thickness from about 10 micron to about 50 micron, such as about 30 micron.

Portions of the conjunctiva 55 can be flexible. Because of this flexibility, injury to a patient can be minor when the conjunctiva 55 is used to secure the surgical contact lens 100 in position. Portions of the conjunctiva 55 can be moved into the slots 135 of the tabs 130 on the lens holder 101 to assist in keeping the surgical contact lens 100 in place during a procedure. For example, as shown in FIG. 1B, a first portion 551 of conjunctiva 55 is positioned in a first slot $\mathbf{135}_1$ on a first tab $\mathbf{130}_1$, and a second portion 552 of conjunctiva 55 is positioned in a second slot $\mathbf{135}_2$ on a second tab $\mathbf{130}_2$.

Referring to FIGS. 1A and 1B, a portion of conjunctiva 55 can be moved into a slot 135 by pushing or entering the portion into the slot 135 from the side surface 133 of the corresponding tab 130. For example, in one embodiment, micro forceps can be used to grab a portion of conjunctiva 55 near a tab 130, the micro forceps and an upper part of the portion of conjunctiva 55 can be moved above the upper surface 132 (shown in FIG. 1E) of the corresponding tab 130, and the portion of conjunctiva 55 can then be pulled into the slot 135 towards the rim 110. In certain embodiments, the width of the slot 135 can be narrower than the width of the portion of conjunctiva 55 moved into the slot 135, making it easier for the slot 135 to retain the portion of conjunctiva 55. In some embodiments, the width of the slot 135 can be from about 5 micron to about 100 micron. Although not shown, in some embodiments, opposing portions of the slot 135, such as sidewalls 136, 137 shown in FIG. 1E, can be configured to contact each other when the slot 135 is empty (e.g., before conjunctiva 55 is positioned in the slot 135). In other words, the slot 135 may be in the form of a slit rather than a triangular or V-shaped opening.

FIG. 1D illustrates a side view of a wide-angle lens 160, according to certain embodiments. The wide-angle lens 160 can be used to view different portions of the patient's eye (e.g., peripheral retina) compared to the lens 150. The lens 160 includes a bottom surface 161 and a side surface 163. The bottom surface 161 can have a curvature configured to conform to an average corneal curvature, a corneal curvature of a particular patient, or an average corneal curvature associated with a group of patients. During some procedures, the lens 150 can be replaced with the wide-angle lens 160 or vice versa while the lens holder 101 remains retained to the patient's eye 50 using the conjunctiva 55 positioned in the slots 135 as shown in FIG. 1B.

Figure 1F:
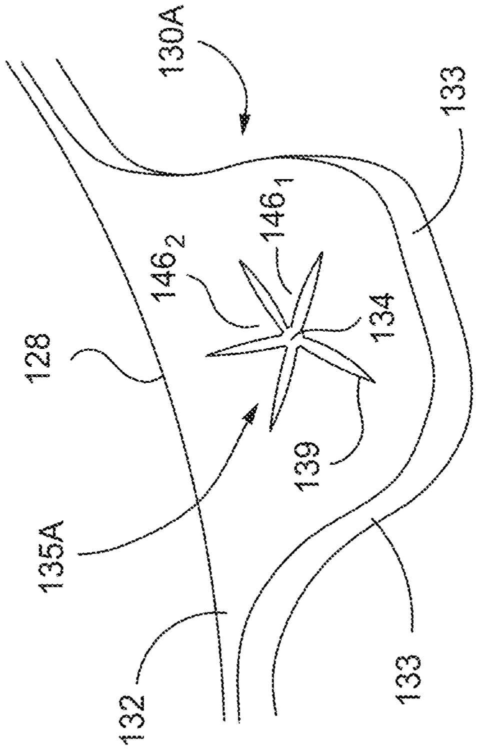
FIG. 1F illustrates a close-up view of an example alternative tab, according to certain embodiments.
Figure 1E:
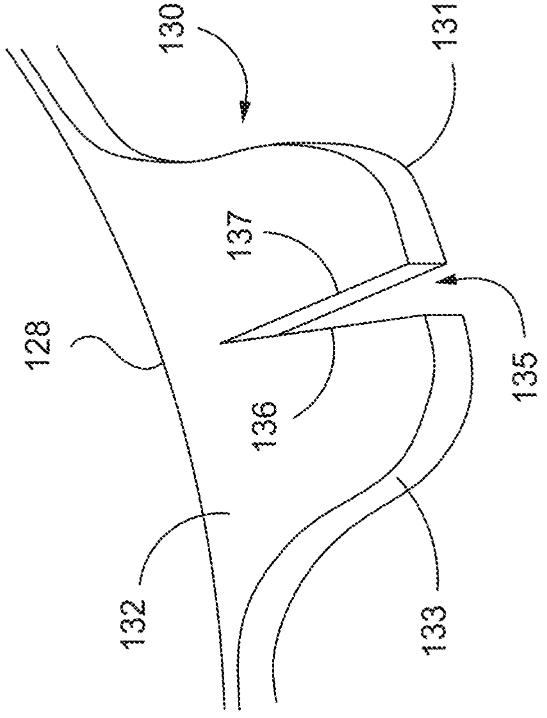
FIG. 1E illustrates a close-up view of the tab shown in section 1E of FIG. 1A, according to certain embodiments.

FIG. 1E illustrates a close-up view of the tab 130 shown in section 1E of FIG. 1A, according to certain embodiments. The tab 130 includes the slot 135 described above. The slot 135 extends out to the side surface 133 of the tab 130. The slot 135 is bounded by opposing sidewalls 136, 137. Each sidewall 136, 137 of the slot 135 extends from the lower surface 131 to the upper surface 132 of the tab 130. The width of the slot 135 can narrow as the distance in the slot 135 from the side surface 133 of the tab 130 increases. This narrowing of the slot 135 can assist in securing a portion of conjunctiva 55 in the slot 135. For example, the deeper into the slot 135 the portion of the conjunctiva 55 is pulled, the more secure the coupling between the slot 135 and the portion of the conjunctiva 55 will be (e.g., because the sides 136, 137 of the slot 135 apply more pressure on the portion of the conjunctiva 55, the deeper the portion is pulled into the slot 135). In certain embodiments, the length of each side 136, 137 is about 1 mm (e.g., range of 0.7-1.3 mm).

FIG. 1F illustrates a close-up view of an alternative tab 130A, according to certain embodiments. The alternative tab 130A can be used on the lens holder 101 in addition to or in place of the tab 130 described above. The tab 130A is the same as the tab 130 described above in reference to FIG. 1E except that the tab 130A includes a different conjunctiva capture feature for securing the conjunctiva 55 instead of the slot 135. The tab 130A includes an opening 135A extending from the lower surface 131 to the upper surface 132 of the tab 130A. The opening 135A is provided in the gaps or areas between a plurality of triangular extensions 146. When there are five triangular extension 146, as shown in FIG. 1F, the opening 135A can have the shape of a thin star. However, a smaller or larger number of triangular extensions can be used. As an example, in certain embodiments, three, four, six, or more triangular extensions 146 can be used. In such embodiments, an opening between the triangular extension may have a shape that is similar to or different from the shape of a star.

In the embodiments of FIG. 1F, the opening 135A includes a central portion 134 and a plurality of narrowing portions 139. Each narrowing portion 139 is provided in between each set of neighboring triangular extensions 146. Each of the plurality of narrowing portions 139 can narrow as a distance from the central portion 134 increases. Each narrowing portion 139 corresponds to an acute angle provided in between each set of neighboring triangular extensions 146 that may be larger or smaller than what is shown in FIG. 1F. Further, in certain embodiments, the acute angles between each set of neighboring triangular extensions 146 may be minimized such that the sides of each triangular extension 146 would be touching or almost touching the corresponding sides of the neighboring triangular extensions 146. In such embodiments, the tip of each of the triangular extension 146 may also touch or almost touch the tips of other triangular extensions 146.

During a procedure, a tool (e.g., micro forceps or a syringe) can be inserted through the central portion 134 and a portion of conjunctiva can be pulled up (e.g., in a proximal direction) through the opening 135A. In some instances, it may be helpful to move the portion of conjunctiva 55 into one of the narrowing portions 139. However, in other instances, the portion of conjunctiva 55 may be thick enough to be secured (e.g., in between the tips of the triangular extension 146) after the portion of conjunctiva 55 is pulled through the opening 135A without any additional manipulation.

Figure 2:
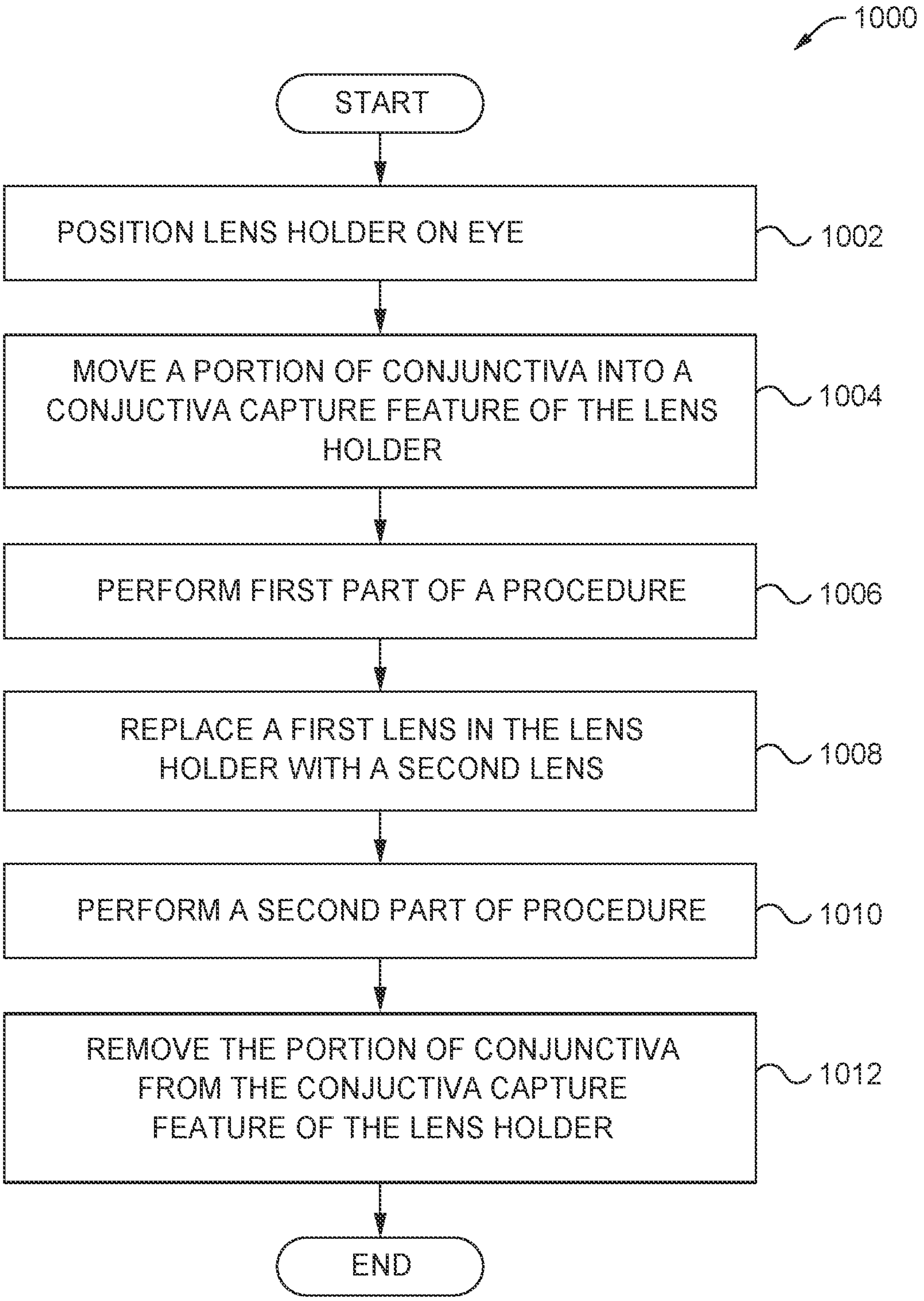
FIG. 2 shows an example process flow diagram of a method for using a surgical contact lens, according to certain embodiments.

FIG. 2 shows an example process flow diagram of a method 1000 for using the lens holder 101 shown in FIG. 1A, according to certain embodiments.

At block 1002, the lens holder 101 is positioned (e.g., by a surgeon) on an ocular surface of a patient's eye 50. A lens, such as the lens 150 may then be positioned in the lens holder 101, such that the bottom surface 151 of the lens 150 is positioned to contact the cornea 51 of the eye 50. In some embodiments, portions of the lower surface 121 of the flange 120 can contact portions of the cornea 51, sclera 52, and conjunctiva 55. In some embodiments, a viscoelastic fluid can be applied between the bottom surface 151 of the lens 150 and/or flange 120 and the surface of the eye 50. The lens holder 101 can be moved on the eye 50 until a targeted position of the lens holder 101 on the eye 50 is achieved.

At block 1004, at least one portion of conjunctiva 55 can be moved (e.g., pulled) into a conjunctiva capture feature of the lens holder 101. As described above, conjunctiva capture feature may be a slot, an opening, or take other forms. The method 1000 of FIG. 2 is described with reference to conjunctiva capture features that take the form of slots, such as the slots 135 shown in FIGS. 1A-1B. However, the lens holder 101 may instead or additionally comprise other types of conjunctiva capture features (e.g., opening 135A), in which case the operations of block 1004 are similarly applicable.

Generally, multiple portions of conjunctiva 55 are moved into separate slots 135 on separate tabs 130 to assist in retaining the lens holder 101 in position. For example, as shown in FIG. 1B, a first portion 551 of conjunctiva 55 can be moved into the first slot $\mathbf{135}_1$ of the first tab $\mathbf{130}_1$, and the second portion 552 of conjunctiva 55 can be moved into the second slot $\mathbf{135}_2$ of the second tab $\mathbf{130}_2$. In some embodiments, a separate portion of conjunctiva 55 can be moved into each of the slots 135 on the lens holder 101. Furthermore, in some embodiments, two or more portions of conjunctiva 55 can be moved into a single slot 135 on the lens holder 101.

A variety of techniques can be used to move the conjunctiva 55 into a slot 135. In some embodiments, micro forceps, a syringe, or another tool can be used to grab a portion of conjunctiva 55 near a tab 130, then the tool and the upper part of the portion of conjunctiva 55 can be moved (e.g., pulled) above the upper surface 132 of the corresponding tab 130, and the portion of conjunctiva 55 can be pulled into the slot 135 to a sufficient depth, such as a depth that would cause the portion of conjunctiva 55 to be adequately retained in the slot 135. After the portion of conjunctiva 55 is positioned to be retained in the slot 135, the portion of conjunctiva 55 can be released by the tool (e.g., micro forceps).

At block 1006, a first part of a procedure is performed on the patient using the surgical contact lens 100 that includes the lens holder 101 and the lens 150. The procedure can vary from an inspection of the eye 50 through the lens 150 to a surgical procedure performed on the eye 50 that is aided by viewing the eye 50 through the lens 150. The conjunctiva 55 retained in the one or more slots 135 can assist in maintaining the position of the lens holder 101 during the first part of the procedure.

At block 1008, the lens 150 is replaced with the wide-angle lens 160 to enable viewing of the eye 50 with the wide-angle lens 160. In some embodiments, a tool (e.g., forceps) can be used to grab the lens 150 to remove the lens 150 from the lens holder 101. In some of these embodiments, the lens 150 is grabbed around the edge 154, for example by accessing the edge 154 through one of the recesses 114 on the rim 110 of the lens holder 101.

After removal of the lens 150, the wide-angle lens 160 can be positioned in the lens holder 101 using a process that is similar to the removal of the lens 150 from the lens holder 101. For example, the lens 160 can be grabbed by its sides, for example using forceps, and positioned inside the lens holder 101. In some embodiments, while positioning the lens 160 inside the lens holder 101, the tip of the forceps can be aligned with the recesses 114 to allow for the lens 160 to be fully positioned and settled in the lens holder 101 without the tip of the forceps colliding with the rim 110.

At block 1010, a second part of the procedure is performed on the patient using a surgical contact lens that includes the lens holder 101 and the wide-angle lens 160. The second procedure can vary from an inspection of the eye 50 through the wide-angle lens 160 to a surgical procedure performed on the eye 50 that is aided by viewing the eye 50 through the wide-angle lens 160. The conjunctiva 55 retained in the one or more slots 135 can assist in maintaining the position of the surgical contact lens 100 during the second part of the procedure.

At block 1012, each portion of conjunctiva 55 positioned in one of the slots 135 can be removed from the corresponding slot 135. For example, the top of each portion of conjunctiva can be grabbed by a tool (e.g., micro forceps) and moved (e.g., pulled) out of the corresponding slot 135. After each portion of conjunctiva 55 that was positioned in a slot 135 is removed from the corresponding slot 135, then the surgical contact lens including the lens holder 101 and the wide-angle lens 160 can be removed from the ocular surface of the patient's eye 50.

Although the disclosure above is directed to securing a lens holder of a surgical contact lens to an eye by moving portions of conjunctiva into a slot on the lens holder, the disclosure can be directed to securing any device or component to an eye in a similar manner. Furthermore, the disclosure of moving the conjunctiva into narrow slots (e.g., slots 135 in FIG. 1A) on tabs of a lens holder is only one method in which conjunctiva can be secured on a device or component, and numerous other techniques are envisioned. For example, an alternative lens holder can include one or more pinch-to-open features (e.g., one feature on each tab) that can grab the conjunctiva after the feature is pinched and then released. In certain embodiments, the pinch-to-open features can each include a portion on an upper surface of a tab (e.g., similar to tabs 130) that can be pinched to open or spread opposing members of the feature on the lower surface of the tab. When the portion on the upper surface is released from the pinch, the opposing members on the lower surface can return to a closed position. As the opposing members return to the closed position, conjunctiva can be grabbed by and wedged between the opposing members to secure the lens holder to the patient's eye.

While the foregoing is directed to embodiments of the present disclosure, other and further embodiments of the disclosure may be devised without departing from the basic scope thereof, and the scope thereof is determined by the claims that follow.

What is claimed is:

1. A lens holder for an ophthalmic procedure, comprising:

a rim configured to hold a removable lens; and a flange coupled to the rim, the flange including a first surface configured to be positioned on an ocular surface of an eye and an opposing second surface, wherein:

the flange includes one or more conjunctiva capture features extending from the first surface to the second surface of the flange, and the one or more conjunctiva capture features comprise one or more slots extending from the first surface to the second surface, the one or more slots comprising a V-shape and are configured to be latched on to one or more portions of conjunctiva of the eye.

2. The lens holder of claim 1, wherein a portion of at least one of the one or more conjunctiva capture features extends to a side surface of the flange.

3. The lens holder of claim 1, wherein at least one of the one or more slots comprises a plurality of triangular extensions providing a central opening through which the one or more portions of the conjunctiva can be pulled in a proximal direction.

4. The lens holder of claim 1, wherein:

the flange includes a ring portion and a plurality of tabs extending outwardly from the ring portion, and at least one of the one or more conjunctiva capture features is provided on one of the plurality of tabs.

5. A surgical contact lens for an ophthalmic procedure, comprising:

a rim;

a lens positioned inside the rim; and a flange coupled to the rim, the flange including a first surface configured to be positioned on an ocular surface of an eye and an opposing second surface, wherein:

the flange includes one or more conjunctiva capture features extending from the first surface to the second surface of the flange, and the one or more conjunctiva capture features comprise one or more slots extending from the first surface to the second surface, the one or more slots comprising a V-shape and are configured to be latched on to one or more portions of conjunctiva of the eye.

6. The surgical contact lens of claim 5, wherein a portion of at least one of the one or more conjunctiva capture features extends to a side surface of the flange.

7. The surgical contact lens of claim 5, wherein:

the flange includes a ring portion and a plurality of tabs extending outwardly from the ring portion, and at least one of the one or more conjunctiva capture features extends through one of the plurality of tabs.

8. The surgical contact lens of claim 5, wherein at least one of the one or more slots comprises a plurality of triangular extensions providing an opening through which the one or more portions of the conjunctiva can be pulled in a proximal direction.

9. The surgical contact lens of claim 5, wherein the lens is removable.

10. A method of securing a contact lens holder to an eye, the method comprising:

positioning a lens holder on an ocular surface of an eye, the lens holder comprising:

a first surface contacting the eye and an opposing second surface, and one or more conjunctiva capture features extending from the first surface to the second surface; and pulling one or more portions of conjunctiva of the eye into at least one of the one or more conjunctiva capture features.

11. The method of claim 10, further comprising:

positioning a first lens inside the lens holder; and replacing the first lens with a second lens.

12. The method of claim 10, further comprising:

releasing the one or more portions of conjunctiva after a corresponding one of the one or more conjunctiva capture features has latched on to the one or more portions of conjunctiva.

* * * * *